US012646097B2

(12) United States Patent　　　　　(10) Patent No.:　US 12,646,097 B2
Aubert et al.　　　　　　　　　　　　(45) Date of Patent:　　Jun. 2, 2026

(54) METHOD FOR DETERMINING A SKIN COLOUR OF A FACE ON BASIS OF NUMERICAL VALUES AND CORRESPONDING SYSTEM

(71) Applicant: L'Oreal, Paris (FR)

(72) Inventors: Johan Aubert, Clichy (FR); Grégoire Charraud, Clichy (FR); Asiya Shakhmametova, Clichy (FR); Louis Dupont De Dinechin, Clichy (FR); Emmanuel Malherbe, Clichy (FR)

(73) Assignee: L'Oreal, Paris (FR)

( * ) Notice: Subject to any disclaimer, the term of this patent is extended or adjusted under 35 U.S.C. 154(b) by 225 days.

(21) Appl. No.: 18/259,915

(22) PCT Filed: Dec. 21, 2021

(86) PCT No.: PCT/EP2021/086979
§ 371 (c)(1),
(2) Date: Jun. 29, 2023

(87) PCT Pub. No.: WO2022/144233
PCT Pub. Date: Jul. 7, 2022

(65) Prior Publication Data
US 2024/0086989 A1　　　Mar. 14, 2024

Related U.S. Application Data

(63) Continuation of application No. 17/139,338, filed on Dec. 31, 2020, now Pat. No. 12,033,202, and a
(Continued)

(30) Foreign Application Priority Data

Feb. 3, 2021　　(FR) ...................................... 2101039

(51) Int. Cl.
*G06Q 30/0601*　　　(2023.01)
*A45D 34/04*　　　　(2006.01)
(Continued)

(52) U.S. Cl.
CPC ......... *G06Q 30/0631* (2013.01); *A45D 34/04* (2013.01); *A45D 34/06* (2013.01);
(Continued)

(58) Field of Classification Search
None
See application file for complete search history.

(56) References Cited

U.S. PATENT DOCUMENTS 8,238,654 B2 * 8/2012 Pan .......................... G09G 5/02
382/167
10,347,163 B1　　7/2019 Herf et al.
(Continued)

FOREIGN PATENT DOCUMENTS

CN　　　101668451 A　　3/2010
CN　　　109152535 A　　1/2019
(Continued)

OTHER PUBLICATIONS

Kips Robin et al., "Beyond Color Correction: Skin Color Estimation in the Wild through Deep Learning," Electronic Imaging (2020), 8 pages.
(Continued)

*Primary Examiner* — Haris Sabah
(74) *Attorney, Agent, or Firm* — Christensen O'Connor Johnson Kindness PLLC

(57)　　　　　　ABSTRACT

This method for determining a skin colour of a region of interest of a user, comprises: —importing, from an image library (LIB) of a user computational device (APP), at least one image (IMk) comprising a representation of the region of interest of the user; —performing processing (TS) of said
(Continued)

at least one image (IMk) with a machine-learning model (AI_TS) suitable for providing, for each imported image (IMk), a numerical value (ClrEstm_k) representative of the skin colour of the region of interest present in said at least None imported image (IMk); —performing evaluation (EVAL) of the skin colour of the region of interest on the basis of said one or more numerical values (ClrEstm_k) of each imported image.

17 Claims, 3 Drawing Sheets

Related U.S. Application Data continuation of application No. 17/139,340, filed on Dec. 31, 2020, now Pat. No. 11,935,107, and a continuation of application No. 17/139,391, filed on Dec. 31, 2020, now Pat. No. 11,478,063, and a continuation of application No. 17/139,454, filed on Dec. 31, 2020, now Pat. No. 11,900,434, and a continuation of application No. 17/139,457, filed on Dec. 31, 2020, now Pat. No. 12,175,516.

(51) Int. Cl.

| | |
|---|---|
| *A45D 34/06* | (2006.01) |
| *A45D 44/00* | (2006.01) |
| *A61K 8/02* | (2006.01) |
| *A61Q 1/02* | (2006.01) |
| *A61Q 1/12* | (2006.01) |
| *A61Q 17/00* | (2006.01) |
| *B08B 3/08* | (2006.01) |
| *G06T 7/90* | (2017.01) |
| *G06T 11/10* | (2026.01) |
| *G06V 10/774* | (2022.01) |
| *G06V 10/82* | (2022.01) |
| *G06V 20/40* | (2022.01) |
| *G06V 40/16* | (2022.01) |
| *H04W 4/80* | (2018.01) |
| *H04W 64/00* | (2009.01) |
| *A45D 34/00* | (2006.01) |
| *G06F 16/9035* | (2019.01) |
| *G06Q 10/40* | (2026.01) |
| *G06T 3/4046* | (2024.01) |
| *H04N 1/60* | (2006.01) |

(52) U.S. Cl.
CPC .............. *A45D 44/005* (2013.01); *A61K 8/02* (2013.01); *A61Q 1/02* (2013.01); *A61Q 1/12* (2013.01); *A61Q 17/005* (2013.01); *B08B 3/08* (2013.01); *G06T 7/90* (2017.01); *G06T 11/10* (2026.01); *G06V 10/774* (2022.01); *G06V 10/82* (2022.01); *G06V 20/40* (2022.01); *G06V 40/161* (2022.01); *G06V 40/169* (2022.01); *G06V 40/171* (2022.01); *H04W 4/80* (2018.02); *H04W 64/006* (2013.01); *A45D 2034/002* (2013.01); *A45D 2034/005* (2013.01); *A45D 2200/058* (2013.01); *A45D 2200/205* (2013.01); *A61K 2800/59* (2013.01); *G06F 16/9035* (2019.01); *G06Q 10/40* (2026.01); *G06Q 30/0643* (2013.01); *G06T 3/4046* (2013.01); *G06T 2207/10016* (2013.01); *G06T 2207/10024* (2013.01); *G06T 2207/30196* (2013.01); *H04N 1/60* (2013.01)

(56) References Cited

U.S. PATENT DOCUMENTS

| | | | | |
|---|---|---|---|---|
| 2003/0090750 A1* | 5/2003 | Takahashi | ........... | H04N 1/6027 |
| | | | | 358/518 |
| 2003/0174215 A1 | 9/2003 | Goldsmith | | |
| 2005/0232482 A1* | 10/2005 | Ikeda | ................... | G06V 40/171 |
| | | | | 382/167 |
| 2007/0065006 A1* | 3/2007 | Wilensky | ............... | H04N 23/88 |
| | | | | 348/E9.04 |
| 2008/0166044 A1* | 7/2008 | Pan | ........................ | G06V 10/56 |
| | | | | 382/167 |
| 2014/0099026 A1 | 4/2014 | Krishnaswamy et al. | | |
| 2018/0255235 A1* | 9/2018 | Tokui | ..................... | H04N 23/61 |
| 2019/0125249 A1* | 5/2019 | Rattner | ................. | G06T 7/0012 |

FOREIGN PATENT DOCUMENTS

| | | |
|---|---|---|
| WO | WO 2008/108760 | 9/2008 |
| WO | WO 2020/118977 | 6/2020 |

OTHER PUBLICATIONS

International Search Report for International Application No. PCT/EP2021/086979, mailed Apr. 22, 2022 (3 pages).
Office Action and Search Report mailed Jul. 26, 2025, issued in corresponding Chinese Application No. 202180080152.5, filed Dec. 21, 2021, 16 pages.
Office Action dated Apr. 1, 2026, in corresponding Chinese Application No. 202180080152.5, (12 pages).

* cited by examiner

METHOD FOR DETERMINING A SKIN COLOUR OF A FACE ON BASIS OF NUMERICAL VALUES AND CORRESPONDING SYSTEM

CROSS-REFERENCES TO RELATED APPLICATIONS

This application is a 371 of PCT/EP2021/086979, filed Dec. 21, 2021, which claims the benefit of FR 2101039, filed Feb. 3, 2021, and U.S. application Ser. No. 17/139,338, filed Dec. 31, 2020, and U.S. application Ser. No. 17/139,340, filed Dec. 31, 2020, and U.S. application Ser. No. 17/139,391, filed Dec. 31, 2020, now U.S. Pat. No. 11,478,063, issued Oct. 25, 2022, and U.S. application Ser. No. 17/139,454, filed Dec. 31, 2020, and U.S. application Ser. No. 17/139,457, filed Dec. 31, 2020, the disclosures of which are incorporated by reference in their entirety.

Modes of implementation and of embodiment of the present invention relate to a method for determining a skin colour of a face, for example but non-limitingly, and a corresponding system, in particular in the context of recommendation of cosmetic products.

Buying products online, especially via mobile computational devices, is a practical way for consumers to navigate and obtain products. Various technologies exist for providing online buyers with recommendations of products liable to interest them according to analyses of their browsing history, purchase history, comments, product scores, etc.

However, there are certain types of product for which an interaction in person is difficult to replace by an online experience. For example, beauty products such as foundations or other make-up products are difficult to search for online, and it is difficult to recommend them in an automated manner. This is mainly due to the fact that the characteristic of the consumer that would be the most relevant basis for a recommendation, i.e. in particular the skin colour of the face, is difficult to estimate in an automated manner. Even if an image or a video of the consumer is captured, this image or video cannot conventionally be used to reliably determine skin colour because of technical limitations in the processing of the images due to uncontrolled environments. Lighting conditions that are inconsistent between the various places would lead to different reproductions of colours in the image or video at different locations, and the determined skin colour would therefore differ according to the lighting conditions.

Patent application PCT/US2020/041350, which was filed on 9 Jul. 2020 and claimed the priority of provisional patent application U.S. Ser. No. 16/516,080, which was filed on 18 Jul. 2019, describes techniques that allow these technical limitations to be overcome in order to accurately estimate skin colour in an image, whatever the lighting conditions.

In particular, patent application PCT/US2020/041350 describes a system that uses at least one machine-learning model to generate an automatic estimation of skin colour. A user has a mobile computational device equipped with a photographic sensor and captures one or more images of his face with the photographic sensor. The mobile computational device transmits the one or more images to a device for determining skin colour that uses one or more machine-learning models to determine skin colour on the basis of the one or more images.

For example, the user may capture a plurality of images by recording a video, instead of one isolated image, and thus modify the lighting conditions by moving the mobile computational device during the capture of the video. Once a plurality of images under various lighting conditions have been provided, the machine-learning model may be used to generate a plurality of determinations of skin colour, which may then be averaged or otherwise combined to improve the accuracy of the determination.

The technique summarized above of patent application PCT/US2020/041350 has drawbacks in so far as the user must himself perform the image capture, this possibly being bothersome or even impossible in certain situations.

It would therefore be desirable to limit the efforts required of the user to accurately determine his skin colour, on the basis of images having diverse and in principle unknown lighting conditions.

In this respect, a method is proposed for determining a skin colour of a region of interest of a user, the face of the user for example, comprising:

importing, from an image library of a user computational device, at least one image comprising a representation of the region of interest of the user;

performing processing of said at least one image with a machine-learning model suitable for providing, for each imported image, a numerical value representative of the skin colour of the region of interest present in said at least one imported image;

performing evaluation of the skin colour of the region of interest on the basis of said one or more numerical values of each imported image.

For example, the user computational device may be a smartphone, a tablet computer, a personal computer, a smartwatch or any other computational device able to have an image library.

By "image library" what is meant is a directory, conventionally provided in user computational devices, that has access to all or almost all of the images and photographs stored in the memory of the user computational device or in a remote memory accessible from the user computational device, a memory of "cloud" type for example.

Said at least one image is preferably a photograph taken with a photographic sensor of the user computational device, and optionally a photograph taken with another device and imported into the user computational device.

It has been noted, surprisingly and unexpectedly, that the machine-learning model pre-trained for the technique summarized above of patent application PCT/US2020/041350, achieves even better results, i.e. results that are more accurate and truer, when the user provides a plurality of images originating from the image library.

Specifically, it turns out that the machine-learning model, although previously trained to process images the lighting conditions of which are modified by movement of the mobile computational device during the capture of a video, performs even better when images the lighting conditions of which are even more diverse and varied, i.e. images such as may exist in the image library of the user computational device, are processed.

Although the invention is particularly advantageously and profitably applicable to determination of the skin colour of a face, it may nevertheless be applied to the determination of the skin colour of another region of interest, for example another part of the body, in particular with a view to applying, to said region of interest, at least one cosmetic product based on said evaluation of the skin colour of this region of interest.

According to one mode of implementation, said at least one image includes metadata timestamping the creation of the respective image (i.e. for example the date and time of the capture of the photograph); and the evaluation of the colour of the skin is carried out on the basis of the numerical value of each image weighted according to a current date and to respective timestamping metadata.

The weighting may correspond to the attribution of an index of confidence to the image, according to the date on which the photograph was taken, for example in order to give, in the evaluation of skin colour, less weight to photographs that are too old or more weight to very recent photographs.

According to one mode of implementation, the numerical value of each image is weighted according to the current date and to respective timestamping metadata so as to take into account a variation in the hue of the skin colour in the course of seasons of the year.

Specifically, the variation in the hue of the skin colour, or in other words tanning, may have a large amplitude in certain people, and is naturally (i.e. ignoring artificial tanning methods) closely correlated with the seasons of the year. Thus, this mode of implementation may for example be provided so as to give less weight to photographs taken in the season opposite to the season of the current date, and to give more weight to photographs taken in the same season as the season of the current date.

Advantageously, the weighting taking account of the variation in the hue of the skin colour in the course of the seasons of the year is carried out so that said evaluation of the skin colour provides a prediction of the skin colour such as it will be subsequently to the current date.

For example, this mode of implementation may be provided so as to give less weight to photographs taken in the seasons preceding the season of the current date, and to give more weight to photographs taken in the seasons following the season of the current date.

According to one mode of implementation, said at least one image includes metadata timestamping the creation of the respective image and/or metadata geolocating the creation of the respective image (i.e. for example GPS coordinates of the place of capture of the photograph); and the processing comprises pre-processing comprising a correction of the colour temperature of each image according to the respective metadata.

Specifically, timestamping and geolocating metadata make it possible to conjecture lighting conditions, with a respective colour temperature for which compensation is to be made. For example, the timestamping metadata may indicate whether a photograph was taken during the day or at night, and the geolocating metadata may further indicate whether the photograph was taken in an inside space or in an outside space.

Advantageously, the correction of the colour temperature of each image is carried out further according to weather-archive data corresponding to the respective metadata, allowing the colour temperature of the lighting conditions of the creation of the respective image to be estimated.

The weather-archive data allow, with certainty, for a given date and a given place, especially daylight and nighttime hours, periods of sunrise and sunset, and insolation conditions to be known. This allows the accuracy of the conjecture as regards lighting conditions to be increased and the correction of colour temperature to be refined.

According to one mode of implementation, in which mode the region of interest of the user is the face of the user, the importing further comprises obtaining a reference image representing a reference face of the user, and the processing comprises pre-processing comprising a selection, via facial recognition, of the reference face in said at least one image imported from the image library of the user computational device.

This makes it possible to avoid the evaluation of skin colour being spoilt by considering various faces of various people in the processing, for example in case of an erroneously imported image, or in case of images containing a plurality of faces.

For example, obtaining the reference image comprises a photographic capture of isolated the region of interest of the user, or an identification by a user of an image representing isolated the region of interest among the images of said image library.

According to one mode of implementation, the machine-learning model is a pre-trained convolutional neural network.

According to one mode of implementation, the method further comprises a recommendation of at least one cosmetic product based on said evaluation of the skin colour of the region of interest.

A system is also provided for determining a skin colour of a region of interest of a user, comprising communication means that are suitable for communicating with a user computational device and that are configured to import, from an image library of the user computational device, at least one image containing a representation of the region of interest of the user. The system comprises processing means configured to perform processing of said at least one image with a machine-learning model suitable for providing, for each imported image, a numerical value representative of the skin colour of the region of interest present in said at least one imported image, and furthermore to perform evaluation of the skin colour of the region of interest on the basis of said one or more numerical values of each imported image.

A system is also provided that comprises communication means that are suitable for communicating with a user computational device and that are configured to implement the importing step of the method such as defined above, and processing means configured to implement the steps of performing processing and evaluation of the method such as defined above.

According to one mode of embodiment, the system further comprises the user computational device configured to communicate to the communication means said at least one image of the image library.

According to one mode of embodiment the communication means are suitable for communicating with the user computational device via a telecommunication network, such as the Internet.

A computer program is also provided comprising instructions that, when the program is executed by a computer, lead the latter to implement the method such as defined above.

A computer-readable medium is also provided comprising instructions that, when they are executed by a computer, lead the latter to implement the method such as defined above.

Other advantages and features of the invention will become apparent on examining the detailed description of completely non-limiting modes of embodiment and of implementation, and the appended drawings, in which:

Figure 1:
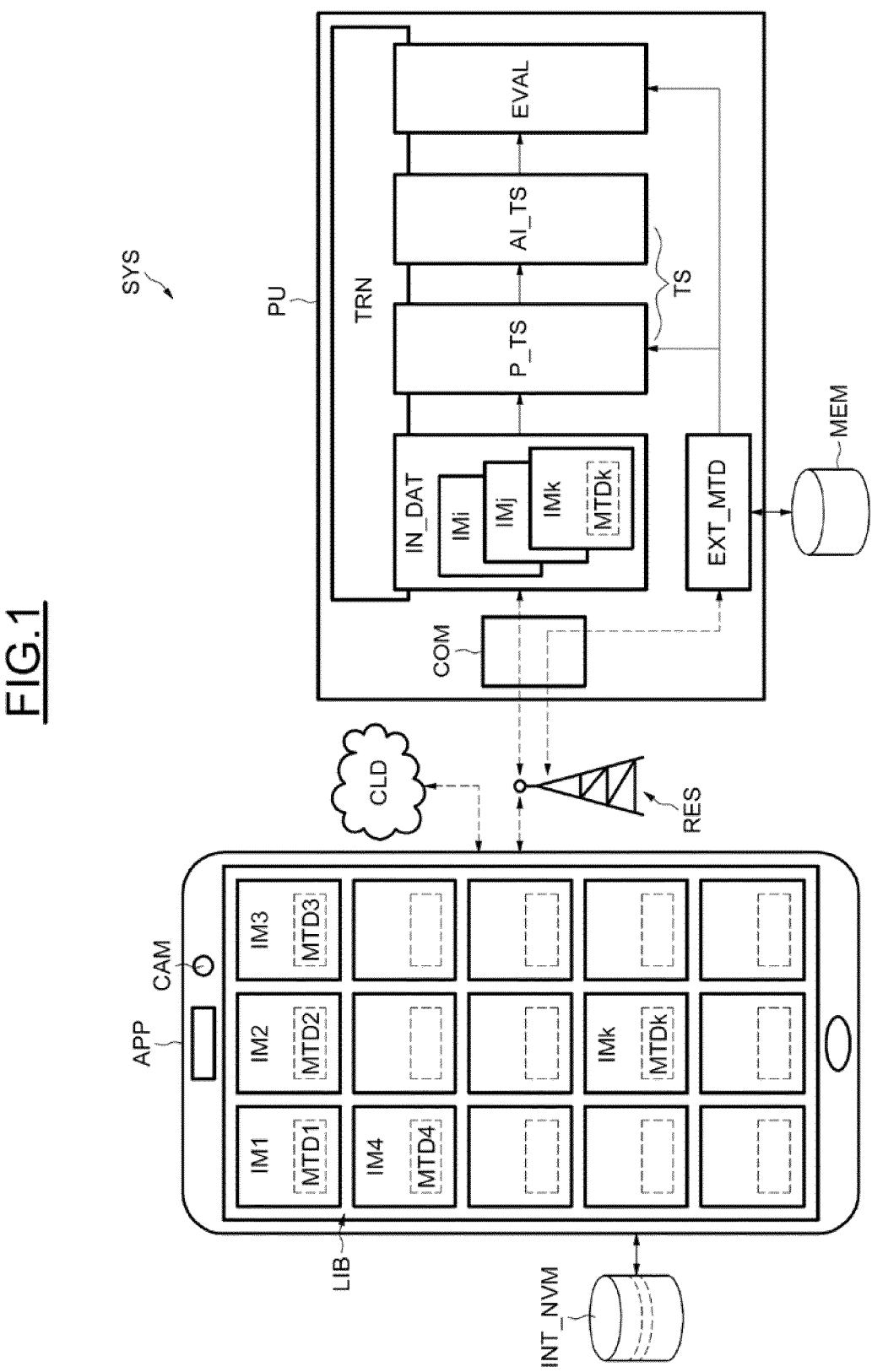
FIG. 1 shows one example of a system SYS comprising processing means PU configured to perform processing TS of said at least one image IMi, IMj, IMk with a machine-learning model AI_TS, and to evaluate EVAL the skin colour of a region of interest of a user, present in the one or more images IMi, IMj, IMk.

For the sake of convenience, and as a result of a non-limiting arbitrary choice, the description is given for the case where the set made up of "said at least one image" is made up of a plurality of images. Implementation in the case where the set made up of "said at least one image" is made up of a single image is analogous in every respect.

For the same reasons, the description is also given with respect to the non-limiting case in which the region of interest of the user is the face of the user.

The machine-learning model is configured and trained to provide, for each image IMk, a numerical value ClrEstm_k representative of the skin colour of a face present in each of the images IMk.

The means for performing evaluation EVAL are configured to evaluate the skin colour of the face on the basis of the numerical values ClrEstm_k of each image. For example, the evaluation may comprise a computation combining the values ClrEstm_k, such as a computation of a mean or median, whether weighted or not.

Communication means COM are suitable for communicating with a user computational device APP and are configured to receive IN_DAT said images IMi, IMj, IMk from an image library LIB of the user computational device APP.

In particular, the user computational device APP may belong to the system SYS in the sense that it may be specifically configured, for example via software, via execution of an application or of a website, to collaborate with the processing means PU with a view to transmitting the images IMi, IMj, IMk during the import IN_DAT of the images by the processing means PU.

The user computational device APP and the communication means COM may communicate using any suitable communication technology, such as wireless communication technologies, for example Wi-Fi, Wi-MAX, Bluetooth, 2G, 3G, 4G, 5G and LTE, or wired communication technologies, for example Ethernet, FireWire and USB. In particular, the user computational device and the device for determining skin colour may communicate at least partially via the Internet.

The user computational device APP may for example be a smartphone, a tablet computer, a personal computer, a smartwatch or any other computational device able to have an image library LIB.

The image library LIB is conventionally a directory provided in the interfaces of user computational devices APP, and which has access to all or almost all of the images and photographs IM1-IM4, IMk stored in an internal non-volatile memory INT_NVM of the user computational device APP. The images and photographs IM1-IM4, IMk of the library LIB may also or alternatively be stored in a remote memory of a server CLD accessible from the user computational device APP (for example in "the cloud" to use the well-known expression).

Said at least one image IM1-IM4, IMk is preferably a photograph, of a face, taken with a photographic sensor CAM of the user computational device APP, or a photograph, of a face, taken with another device and imported into the image library LIB of the user computational device APP.

The images IM1-IM4, IMk of the library of images IMk have a digital image-data format, such as the JPEG format (JPEG standing for Joint Photographic Expert Group), the PNG format (PNG standing for Portable Network Graphics), the GIFF format (GIFF standing for Graphics Interchange Format), the TIFF format (TIFF standing for Tagged Image File Format) or any other image format.

Advantageously, each image IM1-IM4, IMk of the library of images IMk further includes metadata MTD1-MTD4, MTDk providing diverse information regarding the images.

In particular, certain at least of the images IM1-IM4, IMk of the library LIB include timestamping metadata, providing information on the date and time of creation of the respective image, and/or geolocating metadata providing information on the place of creation of the respective image.

As will be seen below with reference to FIG. 2, the timestamping and/or geolocating metadata may allow the processing by the machine-learning model AI_TS and the evaluation EVAL of skin colour to be refined and improved.

The skin colour thus obtained by the machine-learning model AI_TS is true to life and may subsequently be used to recommend one or more cosmetic products that are precisely correlated with the skin colour of each user, in particular foundation, powder and variants of foundation and of powder, and cosmetic products that would complement or would be suitable for the skin colour of the user.

Figure 2:
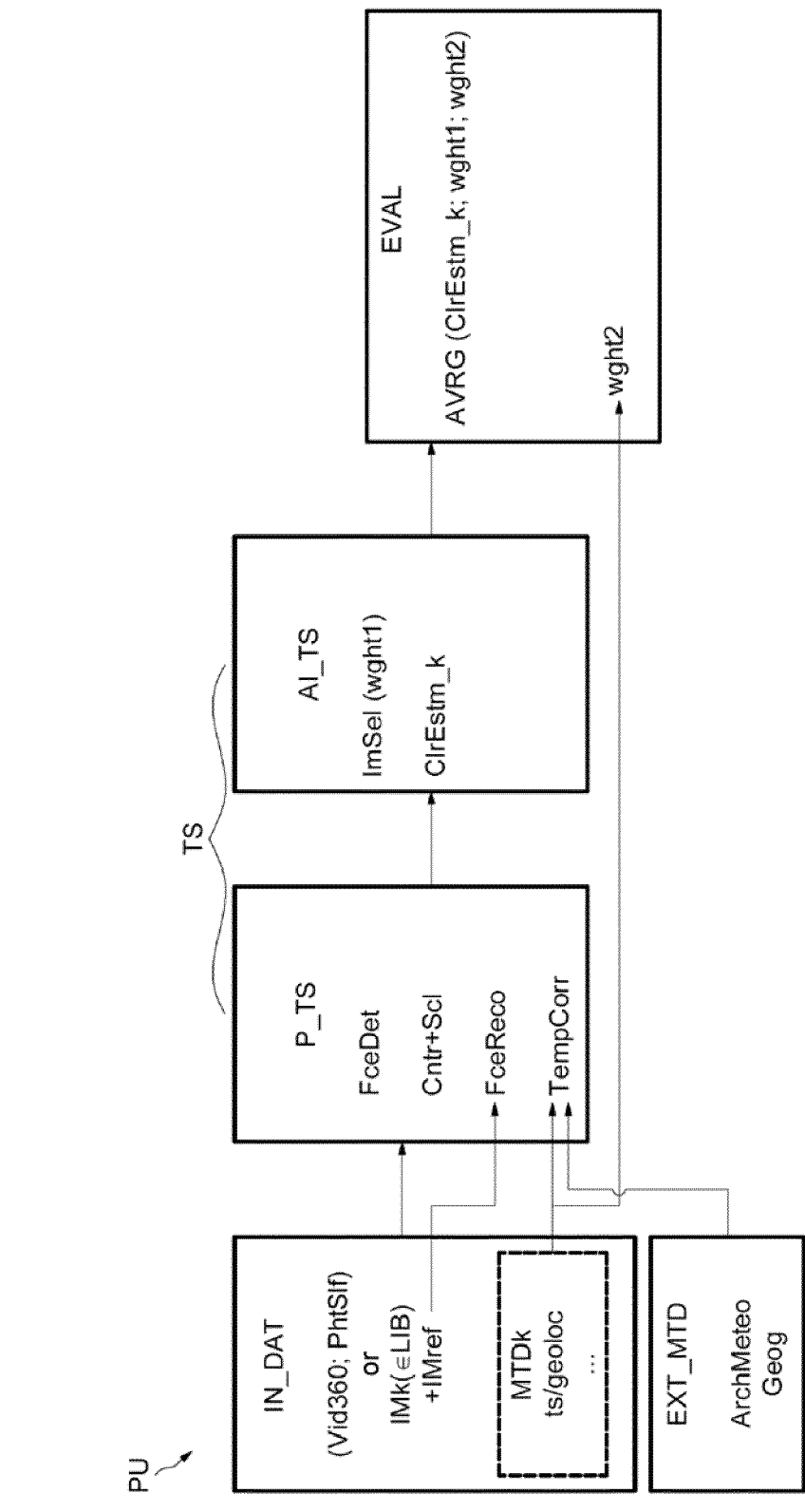

Reference is now made to FIG. 2.

FIG. 2 illustrates one example of a method for determining a skin colour of a face, especially implemented by the processing means PU of the system described with reference to FIG. 1.

The method comprises importing IN_DAT at least one image IMk from the image library LIB of the user computational device, in a way such as described with reference to FIG. 1.

The processing TS, of said at least one image IMk, implemented in this example comprises pre-processing P_TS and processing with a machine-learning model AI_TS that is configured to provide a numerical value ClrEstm_k representative of the skin colour of a face present in said that at least one image IMk.

The pre-processing P_TS comprises converting the images IMk into a format suitable for the machine-learning model AI_TS. In particular, the pre-processing P_TS is suitable for isolating one or more portions of the image containing a face, via a conventional face-detection mechanism FceDet that is known per se, and for centring and scaling Cntr+Scl the portion of the image containing a face, so as to provide normalized data to the machine-learning model.

In short, the centring Cntr may comprise cropping the image so as to preserve only the portion containing the face, and the scaling Scl comprises enlarging or shrinking the cropped image, and under-sampling or over-sampling pixels of the cropped image, so as to provide a cropped image having a set size and a set resolution.

Advantageously, the pre-processing further comprises selecting cropped images containing the same face, via a conventional facial recognition mechanism FceReco that is known per se.

The facial recognition FceReco identifies and detects a target face, i.e. a reference face provided in a reference image IMref. Advantageously, the reference face is isolated in the reference image IMref, i.e. the reference face is the only face present in the reference image IMref.

The reference image IMref may for example be imported from the image library LIB of the user computational device, and be identified to be the reference image IMref by a user. Alternatively, the reference image IMref may be taken by the user by means of the photographic sensor (CAM) of the user computational device, and is advantageously a selfportrait photograph (conventionally "selfie") PhtSlf, so as to comprise isolated the face of the user by way of reference face.

As mentioned above with reference to FIG. 1, the images IMk of the image library advantageously include metadata MTDk. In this case, the pre-processing P_TS may advantageously comprise a correction of the colour temperature TempCorr of the imported images, which correction is established according to the respective metadata MTDk.

Colour temperature is a quantity well known to those skilled in the art, and usually measured in kelvin, that characterizes a light source by comparison to the theoretical principle of thermal radiation of a black body.

Advantageously, the correction of the colour temperature of each image is carried out further according to external data EXT_MTD, such as weather-archive data and geographic data, allowing, in correspondence with the respective metadata MTDk, the colour temperature of the lighting conditions of the creation of the respective image to be estimated.

Specifically, timestamping and geolocating metadata MTDk ts, geoloc make it possible to conjecture lighting conditions, with a respective colour temperature for which compensation is to be made. For example, the timestamping metadata ts may indicate whether a photograph was taken during the day or at night, and the geolocating metadata geoloc may further indicate whether the photograph was taken in an inside space or in an outside space.

The weather-archive data allow, with certainty, for a given date and a given place, especially daylight and nighttime hours, periods of sunrise and sunset, and insolation conditions to be known. This allows the accuracy of the conjecture as regards lighting conditions to be increased and the correction of colour temperature to be refined.

The correction of colour temperature TempCorr by the pre-processing means P_TS may, for example, employ a list of conditions that may be met by the metadata MTDk, external data EXT_MTD optionally being indexed with said metadata MTDk.

A lookup table may possibly allow a specific colour-temperature correction to be selected according to which conditions are met or not.

For example, among simple possible conditions mention may be made of "dawn", "daytime", "night-time", "dusk", "inside", "outside", "clear sky", "cloudy sky", "raining", "snowing", etc. Other conditions, and more complex conditions, may be imagined and conceived of in this respect.

For example, if the metadata MTDk reflect the conditions "night-time" and "inside", then the colour-temperature correction will then possibly be made so as to correct an illumination of the type "inside lighting" or "incandescent bulb". If the metadata MTDk reflect the conditions "dusk", "outside" and "sunlight", then the colour-temperature correction will possibly be made so as to correct an illumination of the setting-sun type.

The mechanism of correction of the colour temperature TempCorr is comparable to a debayering or demosaicing technique, such a technique conventionally being used to individually rebalance the RGB channels of the RAW image captured by the photographic sensor before the image is stored.

This being so, the mechanism of correction of the colour temperature TempCorr advantageously uses a debayering or demosaicing matrix the points of which are tailored according to the conditions, which are evaluated via the metadata MTDk, in the imported images IMk. These adjustments are then consolidated in a static image file that is verified assuming that the colour of one element in the image will always be known (such as for example the white of an eye or to a lesser extent of teeth).

The images IMk thus centred Cntr on a face FceDet, scaled Scl, optionally selected FceReco and optionally corrected TempCorr, are provided to the machine-learning model AI_TS.

The machine-learning model AI_TS computes numerical values ClrEstm_k representative of the skin colour of the face present in each image IMk.

The machine-learning model AI_TS may for example be implemented via a convolutional neural network that is pre-trained, for example in the way described in patent application PCT/US2020/041350, or such as summarized below with reference to FIG. 3. The machine-learning model AI_TS may also be a feed-forward neural network, or a recurrent neural network. Any suitable training technique may be used, especially gradient-descent techniques such as stochastic gradient descent, batch gradient descent and mini-batch gradient descent.

Furthermore, the machine-learning model AI_TS may be capable of selecting conforming images ImSel by detecting aberrant image-capture conditions in the image, such as especially a nonconforming image-capture angle.

This selection of conforming images may be carried out in two stages. Firstly, a machine-learning model allows explicit tests of conditions met to be carried out (example: face looking at the photographic sensor, a single face in the image, a face is indeed in the image). After this first filtering stage, a second selection is made using a quality score wght1, which is for example learnt in a weakly supervised way during the training of the model AI_TS. The quality score wght1 is purely statistical and is especially optimized to improve the accuracy of the model AI_TS during training.

Thus, the machine-learning model AI_TS may assign each result a first weight wght1, especially allowing aberrant results to be discarded.

When the machine-learning model AI_TS has provided the numerical values ClrEstm_k for each image IMk, an evaluation EVAL of the skin colour of the face is carried out on the basis of said numerical values ClrEstm_k and of the respective first weights wght1.

For example, the evaluation EVAL may comprise a computation combining the values ClrEstm_k, such as a computation of a mean or median, weighted with the first weights wght1.

Furthermore, the valuation may advantageously be weighted by second weights wght2, which are obtained on the basis of the metadata MTDk of the respective images, in particular the timestamping metadata ts, in order to take into account a variation in the hue of the skin colour in the course of the seasons of the year, i.e. tanning of the skin.

Specifically, it may be desirable to select photographs taken in the same season as the season of the current date, i.e. of the date on which the skin colour of a face is determined using the disclosed technique.

For example, the weight of images the date of which is that of a season opposite the season of the current date may be decreased using a second weight wght2 of low value, whereas the weight of images the date of which is that of the same season as the season of the current date may be increased using a second weight wght2 of high value.

Advantageously, the second weights wght2 may be determined so that said evaluation EVAL of the skin colour provides a prediction of the skin colour such as it will be subsequently to the current date.

For example, this may be achieved by giving less weight to images the date of which is that of seasons preceding the season of the current date, and by giving more weight to images the date of which is that of seasons following the season of the current date.

Measurements of skin colour with a spectrocolorimeter (or "spectrophotometer") as a function of the season have revealed shifts introduced by summer with respect to winter in average-skin tones. These measurements have allowed macroscopic variations in a population to be established and are integrated into the model of the evaluation EVAL with a view to determining said second weights wght2.

Figure 3:
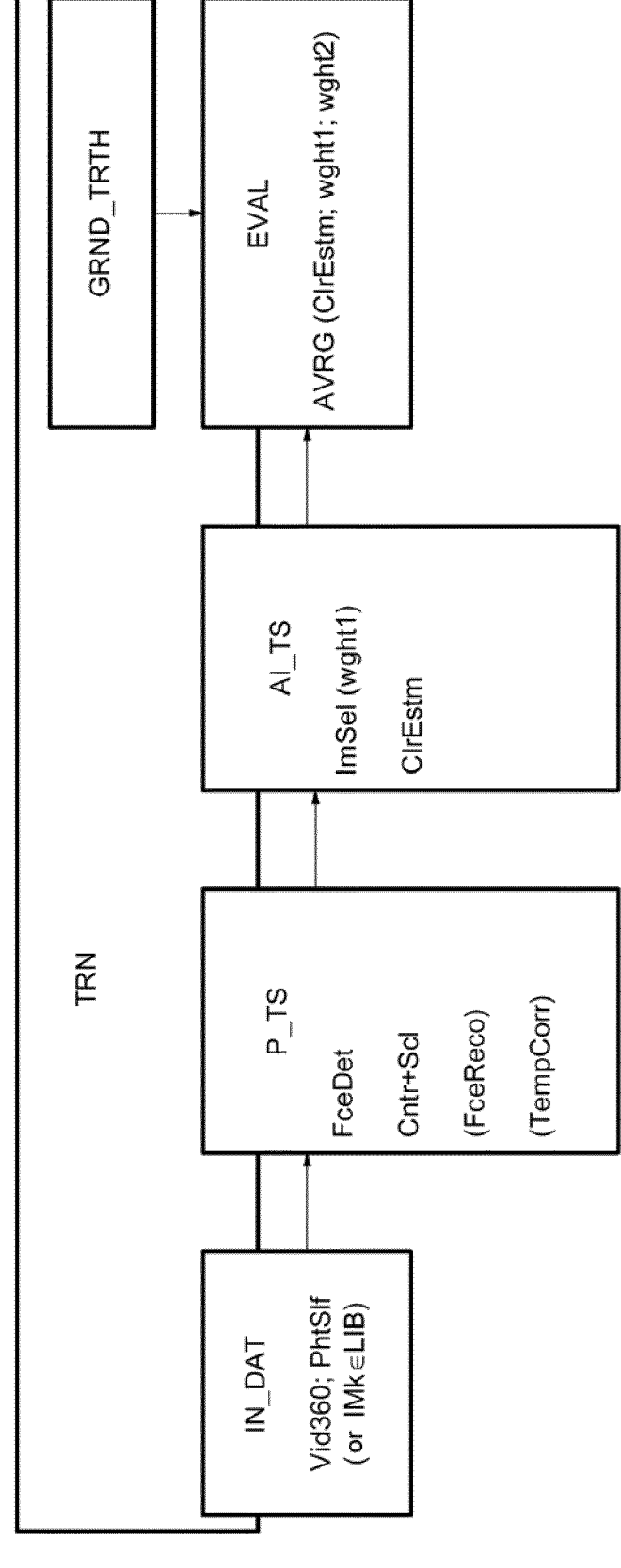
FIG. 3 illustrate modes of embodiment and of implementation of the invention.

FIG. 3 illustrates a non-limiting example of implementation of training TRN of the machine-learning model AI_TS with a view to achieving provision of a numerical value ClrEstm_k representative of the skin colour of a face present in at least one image IMk, such as described above with reference to FIGS. 1 and 2.

The training may be implemented by processing means PU comprising additional training means TRN, especially configured to control the means for receiving data IN_DAT, the pre-processing means P_TS, the machine-learning model AI_TS and the evaluating means EVAL.

A set of training images IN_DAT associated with factual skin colour information GRND_TRTH, which information will be referred to as the "ground truth", are collected for the implementation of the training TRN of the machine-learning model AI_TS.

The ground truth GRND_TRTH as to the skin colour is used as empirical evidence or information to label the images provided by a training subject, i.e. a volunteer, who will be referred to as the panellist.

For example, the ground truth GRND_TRTH may be collected by the user, using a technique for determining skin colour that is standard in the industry, such as comparison with a colour chart or evaluation by a spectrophotometer dedicated to the measurement of skin colours.

In the comparison with a colour chart, one portion of the image may contain a representation of a known reference colour chart, and a correction of the colour of the image that returns the representation of the reference colour chart to its original colours may allow the ground truth GRND_TRTH as to the skin colour present in the image after said colour correction to be determined.

For example, the colour correction that provides the ground truth GRND_TRTH may be implemented in the pre-processing P_TS on command by the training means TRN.

A spectrophotometer may be used at least once on the skin of the panellist, the colour measured by the spectrophotometer possibly being used directly, give or take any translation of the colour code, as the ground truth GRND_TRTH.

The set of training images IN_DAT is provided by the panellist via a user computational device of the same type as the device APP described above with reference to FIG. 1.

For example, the training images IN_DAT are imported via use of the photosensitive sensor CAM of the user computational device of the panellist to capture one or more training images comprising the face of the panellist. The training images may be drawn from individual photographs PhtSlf, for example taken in selfie mode, or from at least one video recording Vid360, for example taken in selfie mode, and in which the lighting conditions may be modified by making the viewpoint move, for example via a rotation of the device around the face of the panellist.

Multiple training images may then be generated by extracting individual images from the video Vid360.

It may be advantageous to capture a video, from which a plurality of training images may be drawn, at least because it will considerably increase the efficiency with which a large amount of training data under various lighting conditions is generated.

Should it be necessary, a skilled person may refer to the description of training of the machine-learning model described in patent application PCT/US2020/041350.

It will be noted that, during the implementation of the training process, the pre-processing P_TS only comprises face detection FceDet and centring and scaling Cntr+Scl such as described above with reference to FIG. 2. Specifically, the assumption that the panellist will provide images only of his face may be made, in which case facial recognition FceReco is not necessary. Furthermore, given that the training images are drawn from photographs or videos, the metadata provide no particular context allowing the correction of colour temperature TempCorr to be parameterized.

Optionally, the training images IN_DAT may in addition or alternatively be drawn from an image library (IMkELIB) of the user computational device of the panellist. In this case, provision may be made to carry out the steps of facial recognition FceReco and of correction of colour temperature TempCorr such as described with reference to FIG. 2.

This being so, it has been noted, surprisingly, that training with only photographs and video recordings, such as mentioned above or indeed such as described in patent application PCT/US2020/041350, provides very satisfactory results in the implementation described with reference to FIG. 2, i.e. in the inference of the machine-learning model AI_TS with images originating from an image library LIB.

In the implementation of the training, the machine-learning model AI_TS executes parameterizable computations on the training images IN_DAT, and provides numerical values ClrEstm representative of the skin colour of a face present in the training images.

The evaluation EVAL of the skin colour may be carried out such as described with reference to FIG. 2, via a statistical operation AVRG that combines the various numerical values ClrEstm.

The skin colour thus evaluated EVAL, or indeed the numerical values ClrEstm directly, are then compared to the ground truth GRND_TRTH in order to re-parameterize the computations executed by the machine-learning model AI_TS in order to get as close as possible to the ground truth.

In other words, the ground truth GRND_TRTH as to the skin colour is used as labelling datum to indicate a desired result of the processing of the training images IN_DAT by the machine-learning model AI_TS.

It will be noted that the machine-learning model AI_TS is advantageously trained with the data of a plurality of panellists. In this respect, the training images IN_DAT and the ground truth GRND_TRTH associated with each panellist may be stored in a memory of the processing means PU and training means TRN. The computation of the machine-learning model AI_TS is parameterized for all of the data of all of the panellists in order to be as universal as possible.

In short, to determine the skin colour of a face, the processing means PU use the machine-learning model AI_TS such as described above to determine the skin colour of the face present in at least one image imported from an image library of a user computational device APP. The skin colour may then be used to recommend one or more cosmetic products that complement or are suitable for the skin colour thus determined.

The invention claimed is:

1. A method for determining a skin colour of a region of interest of a user, comprising:

importing, from an image library (LIB) of a user computational device (APP), at least one image (IMk) comprising a representation of the region of interest of the user;

performing processing (TS) of said at least one image (IMk) with a machine-learning model (AI_TS) suitable for providing, for each imported image (IMk), a numerical value (ClrEstm_k) representative of the skin colour of the region of interest present in said at least one imported image (IMk);

performing evaluation (EVAL) of the skin colour of the region of interest on the basis of said one or more numerical values (ClrEstm_k) of each imported image, the method further comprising a recommendation of at least one cosmetic product based on said evaluation (EVAL) of the skin colour of the region of interest, wherein the at least one image (IMk) includes metadata (MTDk, ts) timestamping the creation of the respective image and/or metadata (MTDk, geoloc) geolocating the creation of the respective image;

wherein the processing (TS) comprises pre-processing (P_TS) comprising a correction of the colour temperature (TempCorr) of each image (IMk) depending on the respective metadata (MTDk).

2. The method according to claim 1, wherein the region of interest of the user is the face of the user.

3. The method according to claim 2, wherein:

the importing further comprises obtaining a reference image (IMref) representing a reference face of the user;

the processing comprises pre-processing (P_TS) comprising a selection, via facial recognition (FceReco), of the reference face in said at least one image (IMk) imported from the image library of the user computational device.

4. The method according to claim 3, wherein obtaining the reference image (IMref) comprises a photographic capture (PhtSlf) of isolated the region of interest of the user, or an identification by the user of an image representing isolated the region of interest among the images (IMk) of said image library.

5. The method according to claim 1, wherein:

said at least one image (IMk) includes metadata (MTDk, ts) timestamping the creation of the respective image;

the evaluation (EVAL) of the skin colour is carried out on the basis of the numerical value of each image (ClrEstm_k) weighted (wght2) according to a current date and to respective timestamping metadata (ts).

6. The method according to claim 5, wherein the numerical value of each image (ClrEstm_k) is weighted (wght2) according to the current date and to respective timestamping metadata (ts) so as to take into account a variation in the hue of the skin colour in the course of seasons of the year.

7. The method according to claim 6, wherein the weighting (wght2) taking account of the variation in the hue of the skin colour in the course of the seasons of the year is carried out so that said evaluation (EVAL) of the skin colour provides a prediction of the skin colour such as it will be subsequently to the current date.

8. The method according to claim 1, wherein the correction of the colour temperature (TempCorr) of each image is carried out further according to weather-archive data (ArchMeteo) corresponding to the respective metadata (MTDk), allowing the colour temperature of the lighting conditions of the creation of the respective image to be estimated.

9. The method according to claim 1, wherein the machine-learning model (AI_TS) is a pre-trained (TRN) convolutional neural network.

10. System A system for determining a skin colour of a region of interest of a user, comprising:

communication means (COM) that are suitable for communicating with a user computational device (APP) and that are configured to import, from an image library (LIB) of the user computational device (APP), at least one image (IMk) comprising a representation of the region of interest of the user, wherein the at least one image (IMk) includes metadata (MTDk, ts) timestamping the creation of the respective image and/or metadata (MTDk, geoloc) geolocating the creation of the respective image;

processing means (PU) configured to perform processing (TS) of said at least one image (IMk) with a machine-learning model (AI_TS) suitable for providing, for each imported image (IMk), a single numerical value (ClrEstm_k) representative of the skin colour of the region of interest present in said at least one imported image (IMk), wherein the processing (TS) comprises pre-processing (P_TS) comprising a correction of the colour temperature (TempCorr) of each image (IMk) depending on the respective metadata (MTDk);

the processing means (PU) furthermore being configured to perform evaluation (EVAL) of the skin colour of the region of interest on the basis of said one or more numerical values (ClrEstm_k) of each imported image, the system being further configured to recommend at least one cosmetic product based on said evaluation (EVAL) of the skin colour of the region of interest.

11. The system according to claim 10, further comprising the user computational device (APP) configured to communicate to the communication means (COM) said at least one image (IMk) of the image library (LIB).

12. The system according to claim 10, wherein the communication means (COM) are suitable for communicating with the user computational device (APP) via a telecommunication network (RES).

13. A non-transitory computer-readable medium comprising instructions that, when they are executed by a computer, cause the computer to perform method steps comprising:

importing, from an image library of a user computational device, at least one image comprising a representation of the region of interest of the user;

performing processing of said at least one image with a machine-learning model suitable for providing, for each imported image, a numerical value representative of the skin colour of the region of interest present in said at least one imported image;

performing evaluation of the skin colour of the region of interest on the basis of said one or more numerical values of each imported image; and generating a recommendation of at least one cosmetic product based on said evaluation of the skin colour of the region of interest, wherein the at least one image includes metadata timestamping the creation of the respective image or metadata geolocating the creation of the respective image;

wherein the processing comprises pre-processing comprising a correction of the colour temperature of each image depending on the respective metadata.

14. A method for determining a skin colour of a region of interest of a user, comprising:

importing, from an image library (LIB) of a user computational device (APP), at least one image (IMk) comprising a representation of the region of interest of the user;

performing processing (TS) of said at least one image (IMk) with a machine-learning model (AI_TS) suitable for providing, for each imported image (IMk), a numerical value (ClrEstm_k) representative of the skin colour of the region of interest present in said at least one imported image (IMk);

performing evaluation (EVAL) of the skin colour of the region of interest on the basis of said one or more numerical values (ClrEstm_k) of each imported image, the method further comprising a recommendation of at least one cosmetic product based on said evaluation (EVAL) of the skin colour of the region of interest;

wherein the at least one image (IMk) includes metadata (MTDk, ts) timestamping the creation of the respective image;

wherein the evaluation (EVAL) of the skin colour is carried out on the basis of the numerical value of each image (ClrEstm_k) weighted (wght2) according to a current date and to respective timestamping metadata (ts).

15. The method according to claim 14, wherein the numerical value of each image (ClrEstm_k) is weighted (wght2) according to the current date and to respective timestamping metadata (ts) so as to take into account a variation in the hue of the skin colour in the course of seasons of the year.

16. The method according to claim 15, wherein the weighting (wght2) taking account of the variation in the hue of the skin colour in the course of the seasons of the year is carried out so that said evaluation (EVAL) of the skin colour provides a prediction of the skin colour such as it will be subsequently to the current date.

17. A system for determining a skin colour of a region of interest of a user, comprising:

communication means (COM) that are suitable for communicating with a user computational device (APP) and that are configured to import, from an image library (LIB) of the user computational device (APP), at least one image (IMk) comprising a representation of the region of interest of the user, at least one image (IMk) includes metadata (MTDk, ts) timestamping the creation of the respective image;

processing means (PU) configured to perform processing (TS) of said at least one image (IMk) with a machine-learning model (AI_TS) suitable for providing, for each imported image (IMk), a single numerical value (ClrEstm_k) representative of the skin colour of the region of interest present in said at least one imported image (IMk), wherein the evaluation (EVAL) of the skin colour is carried out on the basis of the numerical value of each image (ClrEstm_k) weighted (wght2) according to a current date and to respective timestamping metadata (ts);

the processing means (PU) furthermore being configured to perform evaluation (EVAL) of the skin colour of the region of interest on the basis of said one or more numerical values (ClrEstm_k) of each imported image;

the system being further configured to recommend at least one cosmetic product based on said evaluation (EVAL) of the skin colour of the region of interest.

\* \* \* \* \*